(12) United States Patent
Keren

(10) Patent No.: US 6,283,911 B1
(45) Date of Patent: Sep. 4, 2001

(54) RADIATION DELIVERY DEVICES AND METHODS OF MAKING SAME

(75) Inventor: Hanan Keren, Kfar Saba (IL)

(73) Assignee: Medirad I.R.T. Ltd., Kfar Saba (IL)

( * ) Notice: Subject to any disclaimer, the term of this patent is extended or adjusted under 35 U.S.C. 154(b) by 0 days.

(21) Appl. No.: 09/391,054

(22) Filed: Sep. 16, 1999

(30) Foreign Application Priority Data

Sep. 24, 1998 (IL) .................................................. 126341

(51) Int. Cl.[7] ...................................................... A61N 5/00
(52) U.S. Cl. ............................................................ 600/3
(58) Field of Search ....................................... 600/1, 3, 7–8

(56) References Cited

U.S. PATENT DOCUMENTS

| | | | | |
|---|---|---|---|---|
| 5,213,561 | * | 5/1993 | Weinstein et al. | 600/7 |
| 5,302,168 | * | 4/1994 | Hess | 600/3 |
| 5,728,042 | * | 3/1998 | Schwager | 600/3 |
| 6,056,686 | * | 5/2000 | Mawad | 600/3 |
| 6,071,227 | * | 6/2000 | Popowski et al. | 600/3 |
| 6,080,099 | * | 6/2000 | Slater et al. | 600/8 |

* cited by examiner

*Primary Examiner*—John P. Lacyk
*Assistant Examiner*—Joseph A Cadugan

(57) ABSTRACT

A device for delivering radiation to at least one preselected site in a vascular system of a patient, includes an elongated flexible catheter tube of a diameter for insertion into the patient's vascular system, and a flexible guide wire within the catheter tube and movable along its length. The guide wire includes a proximal end to be located externally of the patient's vascular system for moving the guide wire within the catheter tube, and a rounded distal tip at the opposite end to facilitate movement of the guide wire through the catheter tube. At least one radiation-producing element is fixed to the guide wire at an intermediate location spaced from the rounded distal tip.

5 Claims, 5 Drawing Sheets

RADIATION DELIVERY DEVICES AND METHODS OF MAKING SAME

FIELD AND BACKGROUND OF THE INVENTION

The present invention relates to radiation delivery devices, and to methods of making such devices. The invention is particularly useful in coronary revasculization therapy to remove vascular obstructions, and therefore is described below with respect to such an application, but it will be appreciated that the invention could also be used in other applications.

Coronary vascular obstructions generally require coronary bypass surgery, but frequently such an obstruction may be removed or reduced by Percutaneous Coronary Revascularization (PCR), such as by "balloon angioplasty". However, such a PCR treatment frequently results in a renarrowing of the vessel, called "restenosis", triggered by the injury to the vessel wall. Thus, the injury itself may trigger a healing response in the form of growth of a new inner lining within the vessel to heal the injured area ("intimal hyperplasia").

Restenosis is commonly treated today by stenting. It has been found, however, that the provision of a stent may actually increase hyperplasia and thereby aggrevate restenosis, rather than reduce it. Moreover, restenosis following stenting is particularly difficult to treat.

Another technique now being investigated for preventing renarrowing of the vessel caused by hyperplasia is by the use of drugs, but this approach introduces other problems relating to the drug used.

At the present time, the application of radiation appears to be the most promising treatment now being examined for the prevention of restenosis following PCR. Radiation has been found to work particularly well in inhibiting new growth as has been shown for years in cancer management. External beam radiation, administered in relatively high doses, has a damaging effect on the patient's body, and therefore this approach does not appear to be suitable for reducing restenosis. However, using low-dosage radioactive sources, such as seeds temporarily implanted or inserted into the patient's body (endovascular brachytherapy), appears to be a promising treatment for the prevention of restenosis following PCR.

U.S. Pat. No. 5,683,345, which issued Nov. 4, 1997, discloses a technique for utilizing a catheter to deliver a radiation source to a desired site in the vascular system. The radiation source is in the form of a plurality of individually sealed seeds which emit beta radiation. These seeds are stored in a hand-held device and are hydraulically moved through a sterile catheter, inserted into the patient's vascular system, to the site in the vascular system to be treated. However, precisely locating radiation elements when moved in this manner is particularly difficult especially when they are to be located at a plurality of different sites. Also, this technique does not permit shielding those body parts which are not to be irradiated during the passage of the radiation-producing elements to the treatment site.

OBJECTS AND BRIEF SUMMARY OF THE INVENTION

An object of the present invention is to provide another device for delivering radiation to one or more preselected sites in a vascular system of a patient. Another object of the invention is to provide a method of producing such a device.

According to one aspect of the present invention, there is provided a device for delivering radiation to at least one preselected site in a vascular system of a patient, comprising: an elongated flexible catheter tube of a diameter for insertion into the patient's vascular system; a flexible guide wire within the catheter tube and movable along its length, the guide wire including a proximal end to be located externally of the patient's vascular system for moving the guide wire within the catheter tube, and a rounded distal tip at the opposite end of the guide wire to facilitate its movement through the catheter tube; and at least one radiation-producing element fixed to the guide wire at an intermediate location thereof spaced from the rounded distal tip. The radiation-producing element is formed with a slot extending radially from an outer edge to its central region for receiving the flexible guide wire, and for fixing the radiation-producing element to the flexible guide wire.

According to further features in the described preferred embodiments, there are a plurality of the radiation-producing elements positioned along the length of the guide wire for delivering radiation to a plurality of preselected sites along the length of the guide wire.

According to another aspect of the present invention, there is provided a device for delivering radiation to a plurality of preselected sites in a vascular system of a patient, comprising: an elongated flexible catheter tube of a diameter for insertion into the patient's vascular system; a flexible guide wire within the catheter tube and movable along its length, the guide wire including a proximal end to be located externally of the patient's vascular system for moving the guide wire within the catheter tube; and a plurality of radiation-producing elements fixed to the guide wire at the distal end thereof. The device further includes a plurality of non-radiation producing spacer elements fixed to the guide wire between at least some of the radiation-producing elements for spacing the latter elements from each other along the guide wire.

According to a still further aspect of the present invention, there is provided a device for delivering radiation to a plurality of preselected sites in a vascular system of a patient, comprising: an elongated flexible catheter tube of a diameter for insertion into the patient's vascular system; a flexible guide wire within the catheter tube and movable along its length, the guide wire including a proximal end to be located externally of the patient's vascular system for moving the guide wire within the catheter tube; and a plurality of radiation-producing elements fixed to the guide wire at the distal end thereof; each of the radiation-producing elements being of a modular bead-like configuration including a socket section at one end, and a plug section at the opposite end configured to be received with a snap-fit into the socket section of another like radiation-producing element to form a string of such radiation-producing elements; the distal end of the guide wire being formed with a ball received in the socket section of the radiation-producing elements at one end of said string.

As will be described more particularly below, a device constructed in accordance with the foregoing features may be used for accurately delivering radiation to one or more preselected sites in a vascular system for any desired time interval, and may be conveniently removed for reuse after that time interval has expired. In addition, the flexible guide wire may further be provided with a tubular shield normally enclosing each radiation-producing element on the guide wire so as to protect the tissues not to be irradiated. Such shield would be movable longitudinally of the guide wire to uncover and expose selected radiation-producing elements during the treatment process.

Further, at least some of the radiation-producing elements may be separated by dummy elements fixed to the guide wire. Such dummy elements may be of the same configuration as the radial producing elements but not producing radiation. The provision of such dummy elements permits the device to have more uniformity in the construction and manipulatability of the device, but at the same time permits selectivity as to the site or sites in the vascular system to be radiated.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
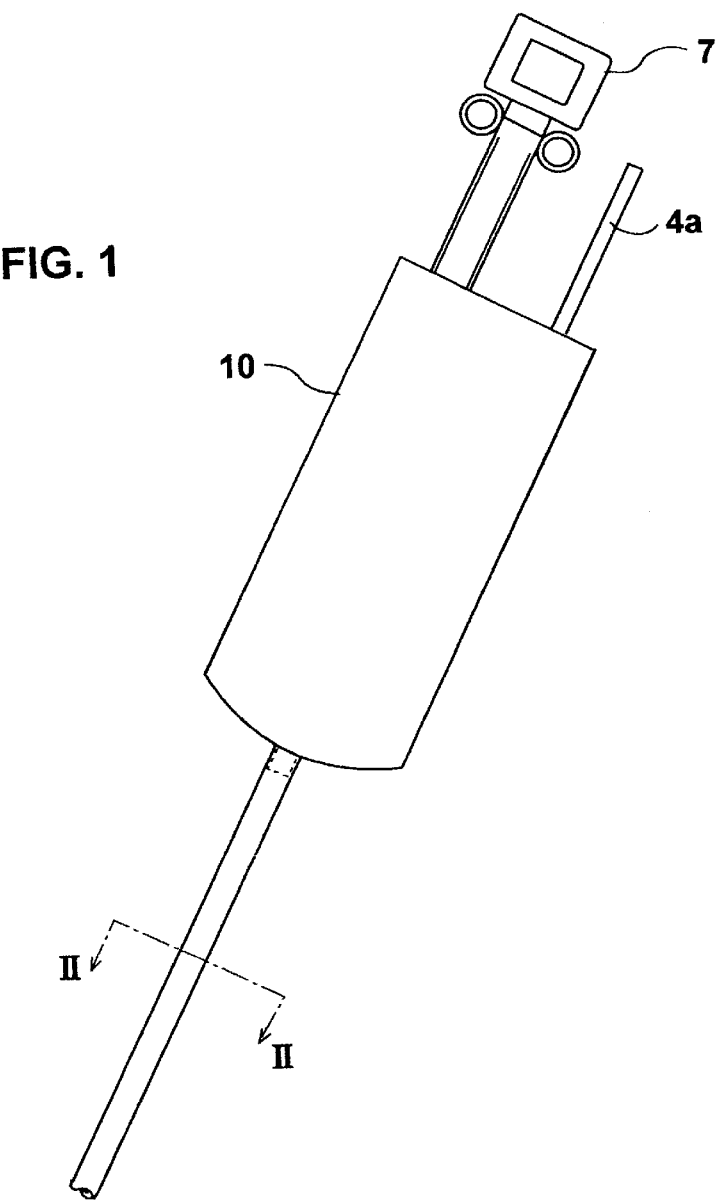
FIG. 1 schematically illustrates one form of catheter device for delivering radiation in accordance with the present invention.

FIG. 1 schematically illustrates one form of catheter-type radiation delivery device constructed in accordance with the present invention. Such a device includes an elongated flexible catheter tube 2 of a diameter for insertion into the patient's vascular system, and a flexible guide wire 4 movable within the catheter tube 2 along its length.

Figure 2:
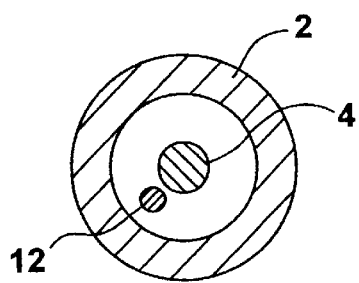
FIG. 2 is a sectional view more particularly illustrating one construction of such a catheter device.

According to one embodiment, the catheter tube 2 and its guide wire 4 may be of the construction illustrated in FIG. 2. Such a construction would be useful where the catheter tube 2 is to be used only for delivering radiation to one or more preselected sites in the vascular system.

Figure 3:
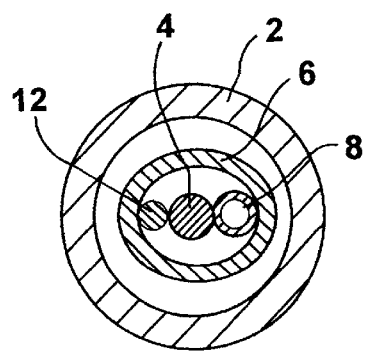
FIG. 3 is a sectional view illustrating another construction of a catheter device that may be used.

FIG. 3 illustrates another embodiment of the invention wherein the catheter tube 2 includes, in addition to the guide wire 4, also an inner catheter tube 6 for carrying a balloon (not shown) to be used in balloon angioplasty for the treatment of a narrowed vessel, by expanding the balloon via pressurized fluid applied, e.g., by an external syringe 7 (FIG. 1), through the lumen 8 in the inner catheter tube 6, in accordance with any of the well known balloon angioplasty techniques. Thus, the catheter construction illustrated in FIG. 3 would be useful where the catheter is first to be used for a balloon angioplasty treatment to reduce vessel narrowing at the preselected site in the vascular system, and then for a radiation-delivering treatment to reduce or prevent vessel renarrowing (restenosis) at that site.

In both constructions, the flexible guide wire 4 is movable along the length of the outer catheter tube 2. Guide wire 4 includes a proximal end 4a, as shown in FIG. 1, to be located externally of the patient's vascular system for moving the guide wire within the catheter tube 2. The distal end of guide wire 4 is shown in FIGS. 4 and 5, wherein it will be seen that its distal tip 4b is rounded to facilitate movement of the guide wire within the catheter tube.

The device illustrated in FIG. 1 further includes a housing 10 for housing the proximal ends of the outer catheter tube 2, the inner guide wire 4, and the inner catheter tube 6 if the device is also to be used for balloon angioplasty. Housing 10 also houses a plurality of radiation-producing elements to be attached to the guide wire 4, and the mechanism for applying the radiation-producing elements to the guide wire 4, as it is fed into the catheter 2.

Figure 4:
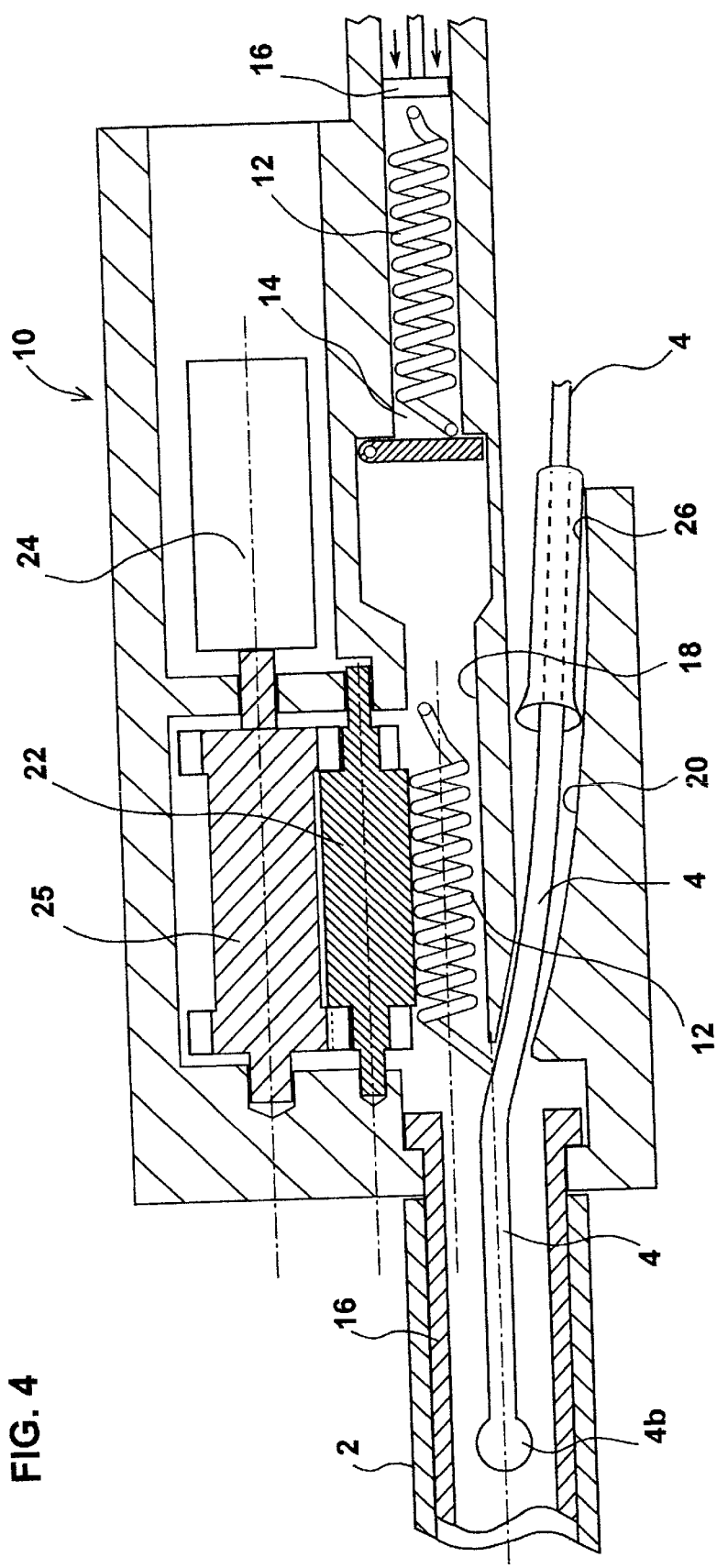
FIG. 4 illustrates one method and apparatus for applying one form of radiation-producing element to the guide wire in the catheter device of FIGS. 1–3 in accordance with the present invention.
Figure 5:
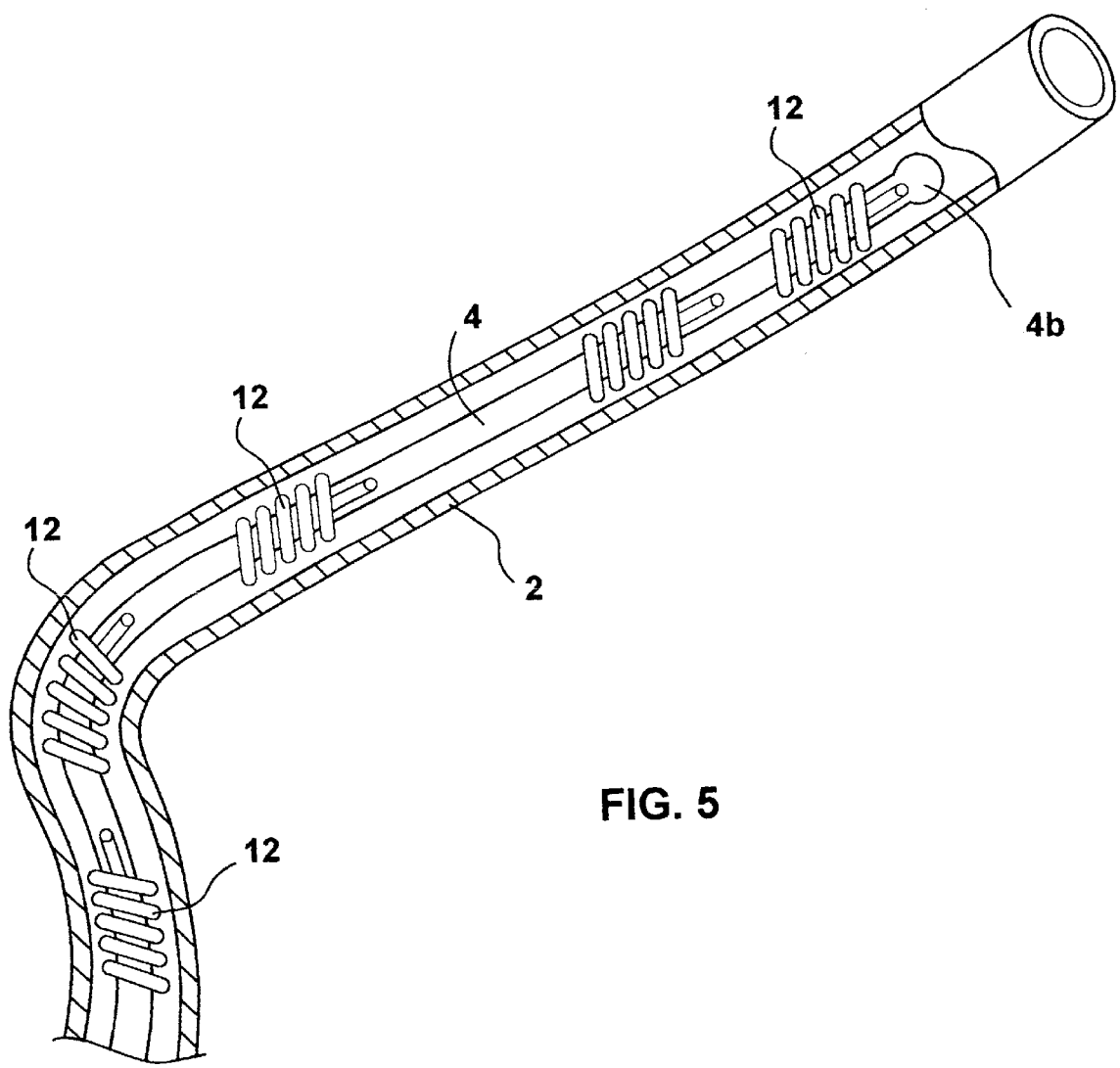
FIG. 5 more particularly illustrates the catheter-type of radiation delivering device produced by the method and apparatus of FIG. 4.

As shown in FIG. 4, the radiation-producing elements are in the form of helical coils 12. They are contained within a storage compartment 14 and are individually fed to the flexible guide wire 4 as the guide wire is fed via a fitting 16 into the catheter tube 2. The helical radiation-producing elements 12 are individually fed, e.g. as schematically shown by plunger 17, into a channel 18 overlying the path 20 of movement of a guide wire 4 towards the catheter tube 2, and are applied to the guide wire by a roller 22 rotated by motor 24 via a gear 25.

It will thus be seen that as guide wire 4 is moved, manually or by a motor (not shown) into the catheter tube 2 (leftwardly, FIG. 4), motor 24 drives roller 22 to rotate each helical radiation-producing element 12 and to wrap that element around the outer surface of the guide wire, and thereby to fix the radiation-producing element to the guide wire. Each such radiation-producing element 12 may thus be fixed to the guide wire at any preselected location by merely controlling motor 24 to apply the element at the appropriate location on the guide wire.

A further important advantage in the illustrated construction is that a shield, shown at 26 in FIG. 4, may be applied over the radiation-producing elements 12 after those elements have been fixed to the flexible guide wire 4. Shield 26 is of tubular configuration and may be made of any suitable shielding material appropriate for the type of radiation produced by elements 12. It would be applied, e.g., via passageway 20, manually or by a motor drive, to loosely enclose all the radiation-producing elements 12, after they have been applied to the flexible guide wire 4, so that the tubular shield may be moved longitudinally with respect to the guide wire in order to uncover and expose selected radiation-producing elements 12 for the radiation treatment.

FIG. 5 illustrates the distal end of the catheter tube 2, and the distal end of guide wire 4 including a plurality of such helical radiation-producing elements 12 applied at spaced locations along the guide wire for radiating the inner surface of the vessel receiving the catheter tube.

After the radiation-producing elements 12 have been used for radiating the preselected site or sites in the patient's vascular system, they may be removed from the guide wire by driving motor 24 in the opposite direction. Roller 22 is thus driven to unthread the helical radiation-producing elements 12 from the guide wire and to shift them back into the storage compartment 14 as the guide wire is moved in the reverse direction through the catheter tube 2.

The helical elements 20 are preferably beta-ray emitters. Examples of materials that may be used for this purpose could include one of the isotopes phosphorous 32 ($^{32}$P), Ytrium 90 ($^{90}$Y), Strontium 90/Ytrium 90 ($^{90}$Sr$^{90}$Y), Rhenium 186 ($^{186}$Re), or Rhenium 188 ($^{188}$Re). Beta-radiation is preferred because of its short range, compared to gamma radiation, and therefore requires considerably less shielding. Also, the use of beta emitters enables the housing 10 to be sufficiently small and light so as to be hand-held.

Making the radiation-producing elements 12 in the illustrated helical configuration better assures that these elements will be self-centered with respect to the guide wire 4, particularly in the arrangement of FIG. 2, so as to more uniformly radiate the complete periphery of the vessel receiving the catheter.

Using the arrangement illustrated in FIG. 3 enables the existing standard angioplasty catheter to be used both for carrying the balloon to expand the vessel, and also for carrying the radiation-producing elements to prevent renarrowing the vessel (restenosis). Thus, after the angioplasty treatment has been performed, the same catheter may be left in the patient's vascular system and used for the irradiation treatment without extracting the catheter and the balloon from the patient's body. A preselected vascular segment may therefore be first subjected to the angioplasty treatment, and immediately thereafter, to the irradiation treatment; and then another vascular segment may be subjected to the angioplasty treatment followed by the irradiation treatment, and so on, without extracting the catheter.

In the conventional angioplasty treatment, the catheter and the balloon are filled with a liquid that would attenuate a large portion of the beta radiation. Preferably, however, the balloon in this case would be filled with a clinically accepted medium characterized by a low radiation-attenuation coefficient to reduce the energy loss on its way to the target tissue. This would significantly shorten the exposure time.

In both constructions of FIGS. 2 and 3, the coils of the helical elements may be formed closer to each other to concentrate the radiation, or moved further apart to spread the radiation over a larger surface. Making the radiation-producing elements 12 of helical configuration also provides flexibility in the guide wire carrying these elements, permitting the guide wire to more easily follow the serpentine path of the catheter tube when introduced into the patient's vascular system.

Figure 6:
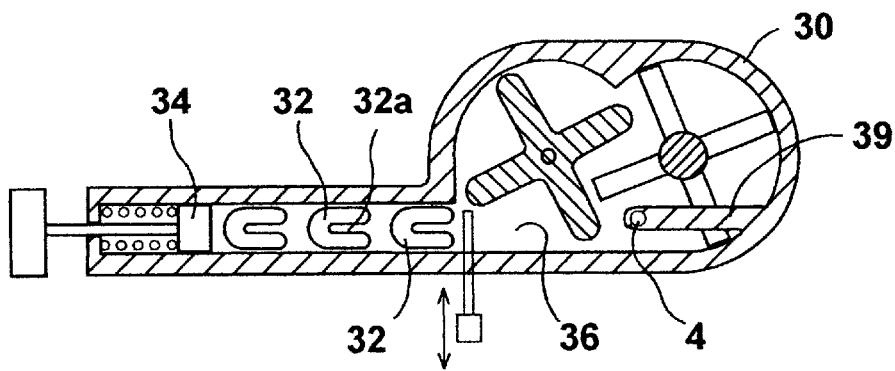
FIGS. 6 and 7 schematically illustrate another method and apparatus for fixing another form of radiation-producing to the guide wire in the catheter-type radiation delivery device.
Figure 7:
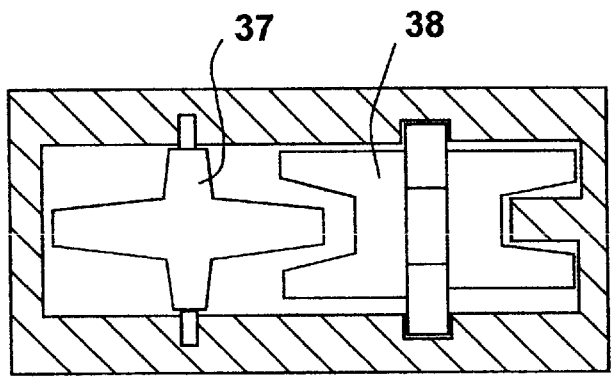

FIGS. 6 and 7 illustrate radiation-producing elements, therein designated 32, of a generally U-shaped configuration, e.g., in the form of a circular disk section but provided with a slot 32a extending radially from one edge to its central region for receiving and fixing the flexible guide wire 4. FIG. 6 schematically illustrates the radiation-producing elements 32 being stored in a hand-held housing 30 and fed by a plunger mechanism, schematically indicated at 34, into compartment 36 of the housing, where they are individually force-fitted onto the guide wire 4 by a pair of toothed wheels 37, 38. As shown in FIG. 6, compartment 36 includes a backing plate 39 engageable with one side of the wire guide 4 as it is fed through that compartment, while the two wheels 37, 38 engage the individual radiation-producing elements 32 and force them onto the opposite side of the guide wire.

Figure 8:
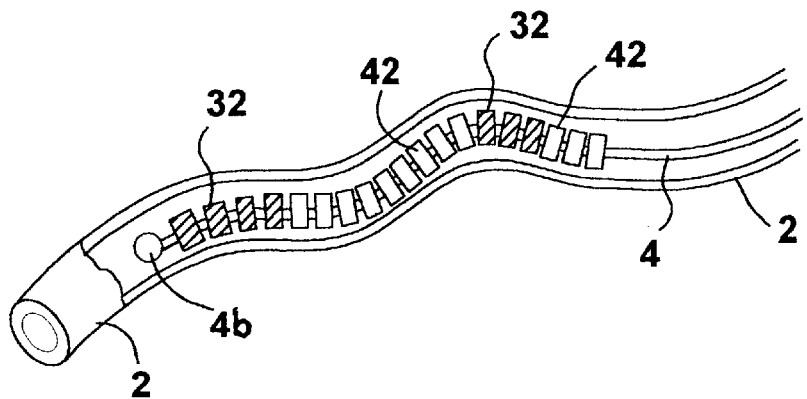
FIG. 8 illustrates the construction of the catheter-type radiation delivery device produced by the method and apparatus of FIGS. 6 and 7.

FIG. 8 illustrates a section of catheter 2 after a plurality of the radiation-producing elements 32 have been applied to its guide wire 4. The radiation-producing elements may be spaced along the length of the guide wire as desired for any particular application. In addition, some of the radiation-producing elements 32 may be separated by dummy elements, shown as 42 in FIG. 8, of the same configuration as the radiation-producing elements 32 but not emitting radiation. Such an arrangement enables the radiation-producing elements 32 to be spaced along the length of the catheter 2 to irradiate preselected vascular segments as may be described for the particular treatment and to still maintain substantial uniformity and manouverablity of the catheter.

Figure 9:
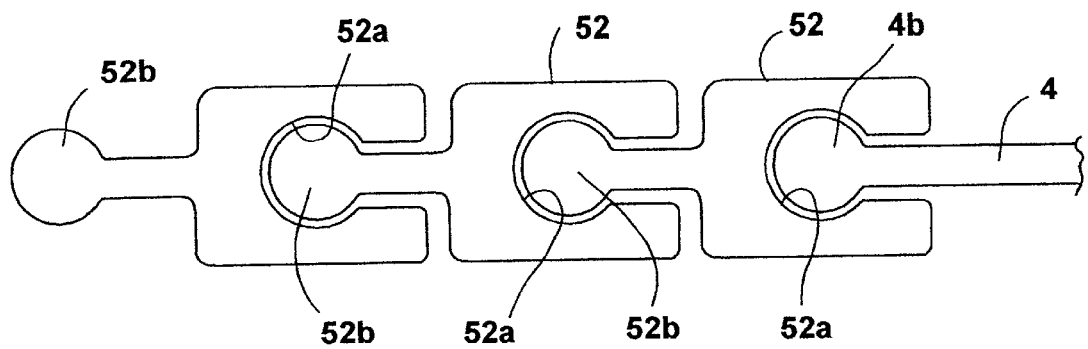
FIG. 9 illustrates another form of radiation-producing elements which may be fixed to the guide wire in the catheter device.

FIG. 9 illustrates a further variation in the configuration of the radiation-producing elements, therein designated 52. In this variation, the radiation-producing elements 52 are of a modular bead-like configuration, each including a socket section 52a at one end and a ball section 52b at the opposite end configured to be received with a snap-fit into the socket section 52a of another like radiation-producing element. In the example illustrated in FIG. 9, the distal end of the guide wire 4 is rounded in the form of a ball, as shown at 4b, so as to be received with a snap-fit into socket section 52a of the first radiation-producing element 52, whereupon the other radiation-producing elements 52 are applied in the same manner, one after the other. The socket sections 52a and the ball sections 52b of these elements are preferably of spherical configuration so as to permit each element to be pivotted in all directions with respect to the adjacent ones, thereby providing the required flexibility to enable the wire guide 4, with these elements attached to be moved through the catheter tube 2.

As described above with respect to FIG. 8, some of the radiation-producing elements 52 in FIG. 9 may also be separated by dummy elements of the same configuration in order to enable the string of radiation-producing elements on the wire guide to deliver the radiation to preselected vascular segments while still maintaining uniformity and manouverability of the string of elements through the catheter tube 2.

Figure 10:
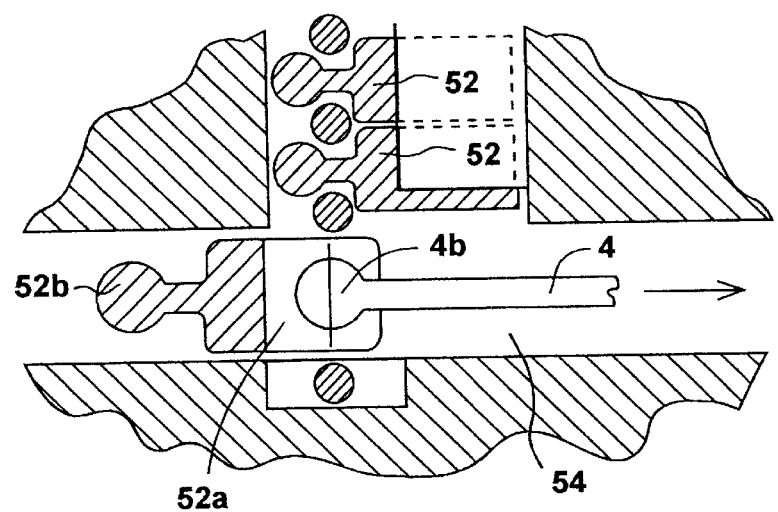
FIG. 10 schematically illustrates one form of apparatus which may be used in producing the device of FIG. 9.

FIG. 10 schematically illustrates one manner of assembling the string of radiation-producing elements. Thus, the radiation-producing elements 52 may be supported in a vertical stack overlying a channel 54 in which the flexible guide wire 4 is moved in stepped increments. Initially, the rounded distal tip 4b of the guide wire 4 overlies the socket section 52a of the lower-most radiation-producing element 52 in the stack, whereupon that element is forced downwardly to snap-fit its section 52a around the rounded distal tip 4b of the flexible guide wire 4. With each additional stepped movement of the guide wire 4, the ball section 52b of the attached radiation-producing element is snap-fitted into the socket section 52a of the next radiation-producing element to be attached.

While the invention has been described with respect to several preferred embodiments, it will be appreciated that these are set forth merely for purposes of example, and that many other variations may be made. For example, the feeding of the catheter tube can be effected by a motor within housing 10 and controlled by a computer also within the housing or outside the housing. When the device is used with balloon angioplasty, the radiation source can be centered within the vessel using either a reduced pressure for the balloon, a profused balloon, or a spiral balloon. In addition, while the invention is particularly useful for treating restenosis in blood vessels it can also be used in other treatments, such as cancer therapy, where it is desirable to deliver a radiation-producing element or elements through passageways, ducts or tubes, to one or more treatment sites within the body.

Many other variations, modifications and applications of the invention will be apparent to those skilled in the art.

What is claimed is:

1. A device for delivering radiation to at least one preselected site in a vascular system of a patient, comprising:

an elongated flexible catheter tube of a diameter for insertion into the patient's vascular system;

a flexible guide wire within said catheter tube and movable along its length, said guide wire including a proximal end to be located externally of the patient's vascular system for moving the guide wire within the catheter tube, and a rounded distal tip at the opposite end of the guide wire to facilitate its movement through the catheter tube;

and at least one radiation-producing element fixed to said guide wire at an intermediate location thereof spaced from said rounded distal tip;

said radiation-producing element being formed with a slot extending radially from an outer edge to its central region for receiving said flexible guide wire and for fixing the radiation-producing element to the flexible guide wire.

2. The device according to claim 1, wherein there are a plurality of radiation-producing elements positioned along the length of the guide wire for delivering radiation to a plurality of preselected sites along the length of the guide wire.

3. The device according to claim 2, wherein each of said radiation-producing elements is of circular configuration and is formed with said radically-extending slot for receiving the guide wire centrally thereof.

4. The device according to claim 3, wherein there are a plurality of said radiation-producing elements of circular configuration spaced from each other along the length of the guide wire.

5. A device for delivering radiation to a plurality of preselected sites in a vascular system of a patient, comprising:

an elongated flexible catheter tube of a diameter for insertion into the patient's vascular system;

a flexible guide wire within said catheter tube and moveable along its length, said guide wire including a distal end to be located within said catheter tube, and a proximal end to be located externally of the catheter tube for moving the guide wire within the catheter tube;

a plurality of radiation-producing elements fixed to said guide wire at the distal end thereof, each of said radiation-producing elements being of circular configuration and being formed with a radial slot for receiving the guide wire centrally thereof;

and a plurality of non-radiation-producing spacer elements fixed to said guide wire between at least some of said radiation-producing elements for spacing said latter elements from each other along said guide wire.

* * * * *